(12) United States Patent  
Moriya

(10) Patent No.: US 8,547,377 B2  
(45) Date of Patent: Oct. 1, 2013

(54) PROJECTION IMAGE GENERATION APPARATUS, METHOD, AND PROGRAM

(75) Inventor: Yoshiyuki Moriya, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 372 days.

(21) Appl. No.: 12/737,022

(22) PCT Filed: Jun. 2, 2009

(86) PCT No.: PCT/JP2009/002479  
§ 371 (c)(1),  
(2), (4) Date: Dec. 2, 2010

(87) PCT Pub. No.: WO2009/147841  
PCT Pub. Date: Dec. 10, 2009

(65) Prior Publication Data  
US 2011/0074785 A1    Mar. 31, 2011

(30) Foreign Application Priority Data  
Jun. 3, 2008    (JP) .................................. 2008-145402

(51) Int. Cl.  
| G06T 15/00 | (2011.01) |
| G06T 17/00 | (2006.01) |
| G06T 15/10 | (2011.01) |
| G06K 9/00  | (2006.01) |
| G06K 9/50  | (2006.01) |
| G06K 9/52  | (2006.01) |

(52) U.S. Cl.  
USPC ........... 345/427; 345/419; 345/424; 382/128; 382/131; 382/201; 382/206

(58) Field of Classification Search  
USPC ................. 382/128, 130–132, 154, 171, 174, 382/190, 201, 206; 345/419, 421–424, 427, 345/649, 650, 652–654, 655, 672, 679  
See application file for complete search history.

(56) References Cited

U.S. PATENT DOCUMENTS

| 5,644,689 A | 7/1997 | Ban et al. |
| 5,734,384 A * | 3/1998 | Yanof et al. ................... 345/424 |

(Continued)

FOREIGN PATENT DOCUMENTS

| JP | 5-189541 | 7/1993 |
| JP | 5-277091 | 10/1993 |

(Continued)

OTHER PUBLICATIONS

Hashimoto Hiroshi, Method for Specifying Three-Dimensional Position of Projected Image, Method for Specifying Volume and Projeced Image Processor, 1999, Machine Translation for Japanese Patent Publication JP 11-203454.*

(Continued)

*Primary Examiner* — Aaron M Richer  
*Assistant Examiner* — Michael J Cobb  
(74) *Attorney, Agent, or Firm* — Jean C. Edwards, Esq.; Edwards Neils PLLC

(57) ABSTRACT

A method for generating a projection image from three-dimensional image data, including the steps of determining first three-dimensional image data to be projected from the three-dimensional image data, generating a first projection image by projecting the first three-dimensional image data in a first projection direction by maximum intensity projection or minimum intensity projection, specifying a first coordinate position in the first projection image, determining second three-dimensional image data to be projected from the three-dimensional image data, generating a second projection image by projecting the second three-dimensional image data in a second projection direction different from the first projection direction, and displaying a second coordinate position, in the second projection image, obtained by projecting a first voxel in the three-dimensional image data, which corresponds to the pixel at the first coordinate position in the first projection image, onto the second projection image from the second projection direction.

9 Claims, 6 Drawing Sheets

(56) References Cited

U.S. PATENT DOCUMENTS

| | | | |
|---|---|---|---|
| 6,674,894 B1 * | 1/2004 | Parker et al. | 382/154 |
| 2002/0068863 A1 | 6/2002 | Slack | |
| 2003/0132933 A1 * | 7/2003 | Kim | 345/419 |
| 2005/0110748 A1 | 5/2005 | Boeing et al. | |
| 2005/0180540 A1 * | 8/2005 | Mukumoto | 378/4 |
| 2006/0071930 A1 * | 4/2006 | Fujiwara et al. | 345/419 |
| 2006/0262969 A1 * | 11/2006 | Matsumoto | 382/131 |
| 2006/0285738 A1 | 12/2006 | Boese et al. | |
| 2007/0189448 A1 * | 8/2007 | Muller et al. | 378/37 |
| 2007/0237379 A1 * | 10/2007 | Haque et al. | 382/130 |
| 2010/0215225 A1 * | 8/2010 | Kadomura et al. | 382/128 |

FOREIGN PATENT DOCUMENTS

| | | |
|---|---|---|
| JP | 7-262352 | 10/1995 |
| JP | 11-203454 | 7/1999 |
| JP | 2001-149366 A | 6/2001 |
| JP | 2002-330958 | 11/2002 |
| JP | 2005-322257 | 11/2005 |

OTHER PUBLICATIONS

D.L. Parker, "Image Segmentation Based Upon the Maximum Intensity Projection Z-Buffer", Proc. Intl. Sot. Mag. Reson. Med. May 8, 2000, p. 535.

* cited by examiner

PROJECTION IMAGE GENERATION APPARATUS, METHOD, AND PROGRAM

CROSS-REFERENCE TO RELATED APPLICATIONS

The present invention is a 35 USC 371 national stage entry of PCT/JP2009/002479, filed Jun. 2, 2009, which claims priority from Japanese Patent Application No. 2008-145402, filed Jun. 3, 2008, the contents of all of which are herein incorporated by reference in their entirety.

BACKGROUND OF THE INVENTION

1. Technical Field

The present invention relates to an apparatus and method for tracking and displaying a point of attention in a projection image generated from three-dimensional image data, and more specifically to a projection image generation apparatus, method, and program for tracking and displaying, when an area of attention is specified in a projection image, the area of attention in another projection image generated by changing the projection direction.

2. Description of the Related Art

When observing a plurality of medical tomographic images obtained by CT (computed tomography), MRI (nuclear magnetic resonance imaging machine), or the like, it has been widely practiced to generate a projection image by, for example, maximum intensity projection from three-dimensional image data obtained by stacking tomographic images that include an area of attention for observation, because it takes a long time to observe all of the tomographic images one by one and it requires a lot of skill for a doctor to understand a three-dimensional shape of an observation target organ or tissue based only on the tomographic images.

But, front-back information of three-dimensional image data in the projection direction is lost in a maximum intensity projection image, so that a first projection image obtained by performing imaging from a first projection direction alone may not sometimes tell the anteroposterior relationship of organs or tissues in the projection direction represented by the projection image. Consequently, doctors make a comparison between the first projection image and a second projection image (even a third projection image) obtained from a second projection direction (third projection direction) different from the first projection direction to understand a three-dimensional anteroposterior relationship (front-back relationship) of regions of attention.

Japanese Unexamined Patent Publication No. 5 (1993)-189541 proposes a user interface used when generating an image of an object represented as a three-dimensional image projected from a different viewpoint for rotating the object in a sense which is similar to operating the object in a real space (here, the change of projection direction and the rotation of the target object are synonymous). Further, in a case where a projection image is obtained by maximum intensity projection, Japanese Unexamined Patent Publication No. 5 (1993)-277091 proposes a method for spuriously representing a three-dimensional positional relationship, when generating a projection image of blood vessels by subjecting three-dimensional image data obtained by MRA (magnetic resonance angiography) to maximum intensity projection, by detecting an intersection between two or more blood vessels to detect the anteroposterior relationship (front-back relationship) of intersecting blood vessels and decreasing the luminance value of the blood vessel on the back side.

The projection image observation using the conventional methods described above, however, still has a problem that the front-back relationship of organs or tissues of attention in the projection direction in a maximum intensity projection image is difficult to understand. In particular, when observing projection images generated from the second and third projection directions, there has been a problem that where the area of attention in the first projection image is moved in the second or third projection image, or otherwise whether or not the area of attention in the first projection image is displayed in the second or third projection image.

In view of the circumstances described above, it is an object of the present invention to provide an apparatus, method, and program capable of obtaining and displaying, when a point is specified in a first projection image, a position of a first voxel in three-dimensional image data corresponding to the point in a second projection image generated from a projection direction different from that of the first projection image.

It is a further object of the present invention to provide an apparatus, method, and program capable of clearly indicating that, when the first voxel described above and a second voxel in three-dimensional image corresponding to the pixel of the coordinate position in a second projection image to which the first voxel is projected are different, the first and second voxels are different.

SUMMARY OF THE INVENTION

A projection image generation apparatus of the present invention is an apparatus for generating a projection image by processing three-dimensional image data obtained by reconstructing multiple two-dimensional images, the apparatus including a first projection target determination means for determining first three-dimensional image data to be projected from the three-dimensional image data, a first projection image generation means for generating a first projection image by projecting the first three-dimensional image data in a first projection direction by maximum intensity projection or minimum intensity projection, a first coordinate specifying means for specifying a first coordinate position in the first projection image, a second projection target determination means for determining second three-dimensional image data to be projected from the three-dimensional image data, a second projection image generation means for generating a second projection image by projecting the second three-dimensional image data in a second projection direction different from the first projection direction, and a second coordinate display means for displaying a second coordinate position, in the second projection image, obtained by projecting a first voxel in the three-dimensional image data, which corresponds to the pixel at the first coordinate position in the first projection image, onto the second projection image in the second projection direction.

A projection image generation method of the present invention is a method for generating a projection image by processing three-dimensional image data obtained by reconstructing multiple two-dimensional images, the method including the steps of specifying an area of interest in a first projection image generated from a first projection direction, determining a voxel in the three-dimensional image data corresponding to the specified area, and displaying, in a second projection image generated from a second projection direction different from the first projection direction, a coordinate position obtained by projecting the voxel in the three-dimensional image data corresponding to the specified area in the second projection direction. In particular, the method is designed, when the area of attention specified in the first projection image is not projected in the second projection image, to indicate so.

Here, the term "area of interest" as used herein refers to a region of interest displayed on a projection image, and the area of interest may be one pixel point or a certain area including an adjacent area of the pixel point.

That is, the projection image generation method of the present invention is a method for generating a projection image by processing three-dimensional image data obtained by reconstructing multiple two-dimensional images, the method comprising the steps of determining first three-dimensional image data to be projected from the three-dimensional image data, generating a first projection image by projecting the first three-dimensional image data in a first projection direction by maximum intensity projection or minimum intensity projection, specifying a first coordinate position in the first projection image, determining second three-dimensional image data to be projected from the three-dimensional image data, generating a second projection image by projecting the second three-dimensional image data in a second projection direction different from the first projection direction, and displaying a second coordinate position, in the second projection image, obtained by projecting a first voxel in the three-dimensional image data, which corresponds to the pixel at the first coordinate position in the first projection image, onto the second projection image in the second projection direction.

The projection image generation method of the present invention may be provided as a program to be executed by a computer recorded on a computer readable recording medium.

According to the projection image generation apparatus, method, and program of the present invention, the position to which the voxel in three-dimensional image data corresponding to the area specified in the first projection image generated from three-dimensional image data is projected can be displayed in the second projection image generated from a projection direction different from that of the first projection image. Further, the invention may also indicate whether or not the voxel of the area specified in the first projection image is displayed in the second projection image. Consequently, a three-dimensional positional relationship of organs or tissues of attention can be easily known from the projection images.

DESCRIPTION OF THE INVENTION

Hereinafter, embodiments of the present invention will be described in detail with reference to the accompanying drawings.

Figure 1:
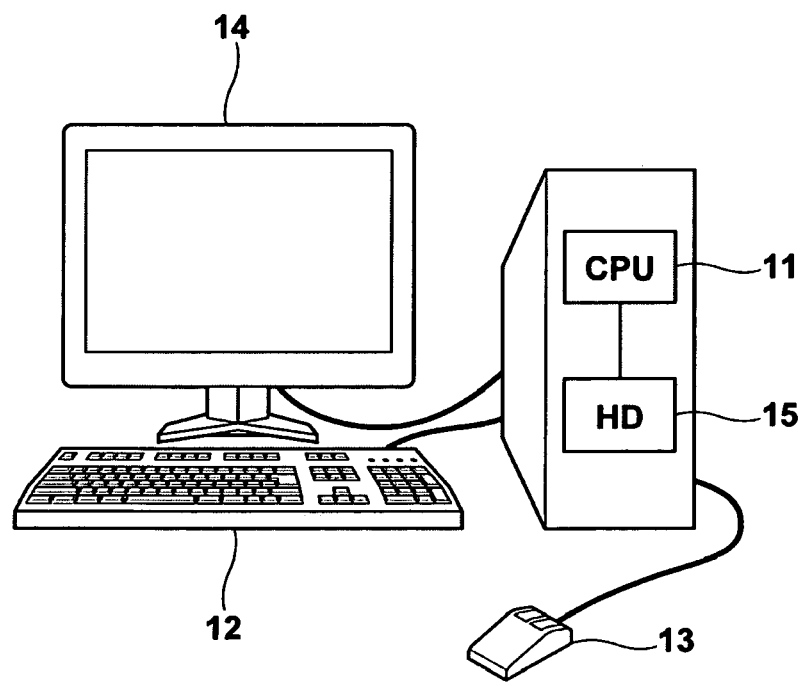
FIG. 1 is a block diagram of a point of attention tracking and displaying apparatus according to a first embodiment of the present invention, illustrating the configuration thereof.

FIG. 1 is a schematic block diagram of a projection image generation apparatus, that is, a tracking and displaying apparatus for a point of attention in a projection image, illustrating a configuration thereof. The point of attention tracking and displaying apparatus of the first embodiment includes keyboard 12 and mouse 13 for accepting a user operation and user input, CPU 11 for performing various image data input/output controls, accepting input from keyboard 12 and mouse 13, and executing a program for implementing the method of the present invention, monitor 14 for displaying an image which can be obtained in the present invention, and hard disk 15 for storing processing target three-dimensional image data in the present invention and a program for executing the method of the present invention, as shown in FIG. 1. Note that a configuration may be adopted here in which the processing target three-dimensional image data are stored in a server linked to the point of attention tracking and displaying apparatus and data are transferred to the apparatus as required.

Three-dimensional image data to be inputted are data of a plurality of brain tomographic images in a body axis direction obtained by MRI and a three-dimensional shape of a brain blood vessel is observed by a doctor using an image projected by maximum intensity projection. Here, a central projection method and a parallel projection method are known, and the parallel projection method is used in the present embodiment to generate a projection image.

Figure 2:
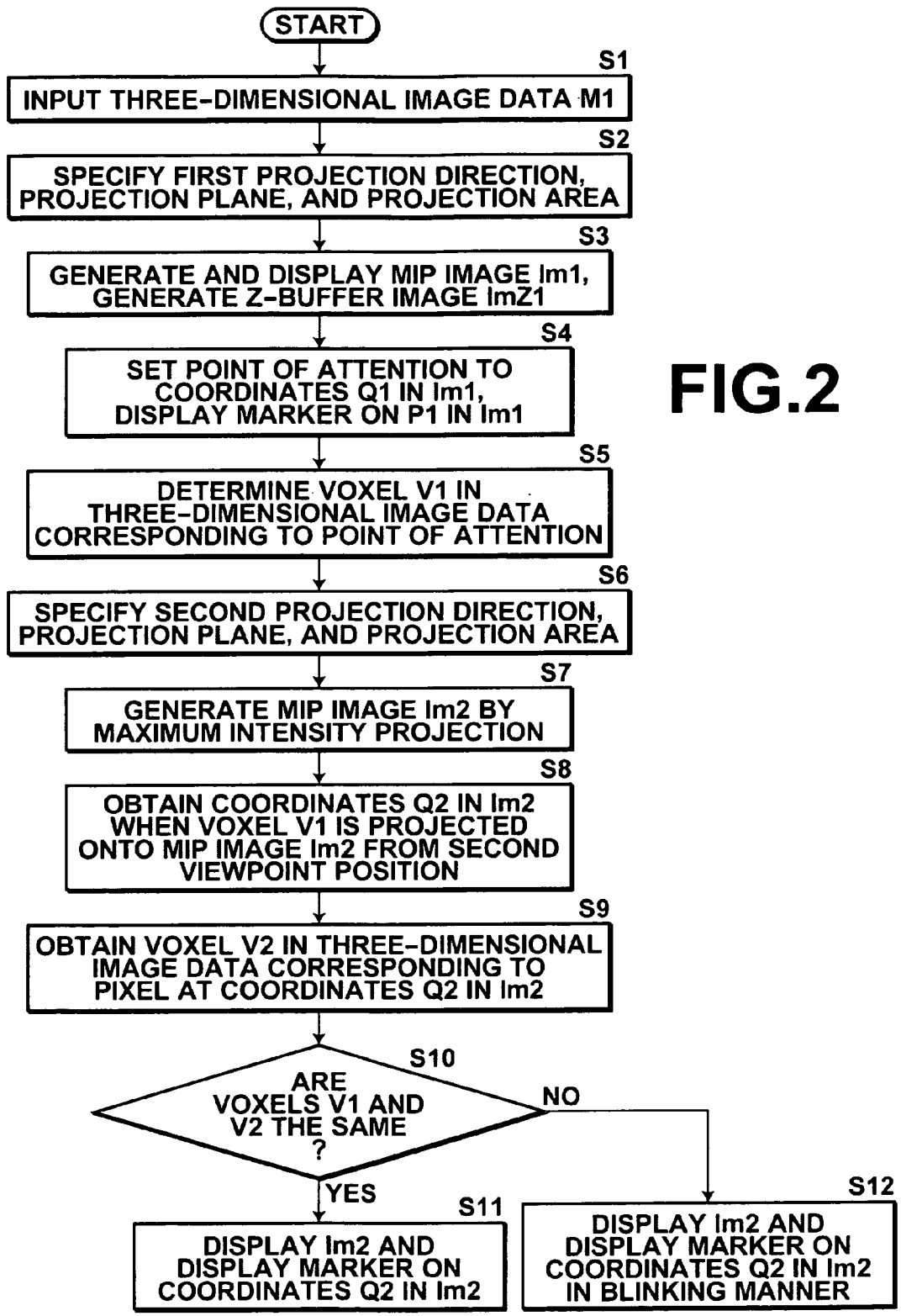
FIG. 2 is a flowchart illustrating a process performed by a point of attention tracking and displaying method according to the first embodiment of the present invention.

FIG. 2 is a flowchart illustrating a process performed by a point of attention tracking and displaying method in a maximum intensity projection image (MIP image) according to the first embodiment of the present invention.

Figure 3:
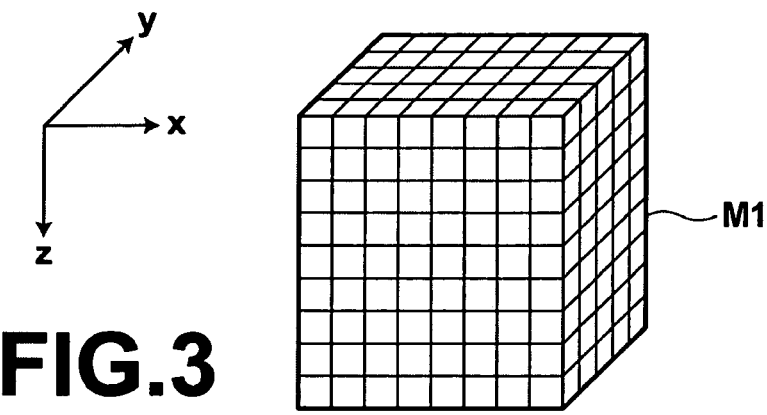
FIG. 3 is a drawing for explaining three-dimensional image data to be processed.

In Step S1, three-dimensional image data M1 obtained by stacking a plurality of tomographic images captured by MRI are inputted. The three-dimensional image data M1 are formed of each voxel, as shown in FIG. 3. When the slice interval of tomographic images obtained by MRI is large, the three-dimensional image data M1 may be interpolated in order to obtain more detailed voxel data. If an area of the three-dimensional image data M1 to be observed is already determined, the projection area may be set, for example, only to a left brain in Step 51.

Figure 4:
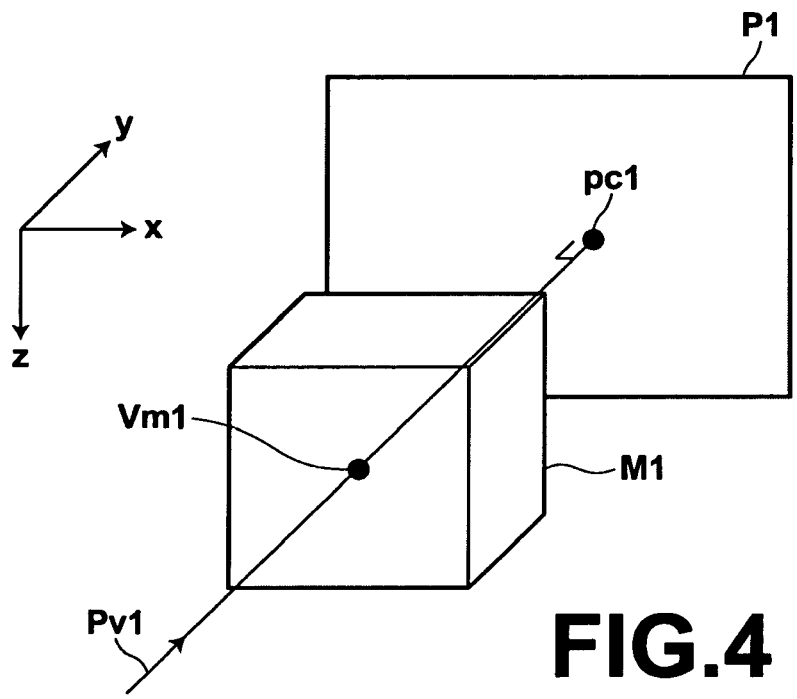
FIG. 4 is a drawing for explaining an initial projection direction and a determination of projection plane in the point of attention tracking and displaying method according to the first embodiment of the present invention.

Next, in Step S2, a first projection direction vector Pv1, a projection plane P1, and a projection target voxel are determined in order to generate a first MIP image Im1, as illustrated in FIG. 4. Here, it is the generation of an initial MIP image, so that a y-axis direction is determined to be the first projection direction vector Pv1. After the first projection direction vector Pv1 is determined, the first projection plane P1 with the first projection direction vector Pv1 as its normal is determined. Then, a projection target voxel is determined from the three-dimensional image data M1. In the present example, the projection target voxel is the entirety of the three-dimensional imaged data M1, but the user may determine the projection target voxel, for example, by a means of manually cutting out only voxel data adjacent to a blood vessel desired to be observed from the three-dimensional imaged data M1.

Figure 7:
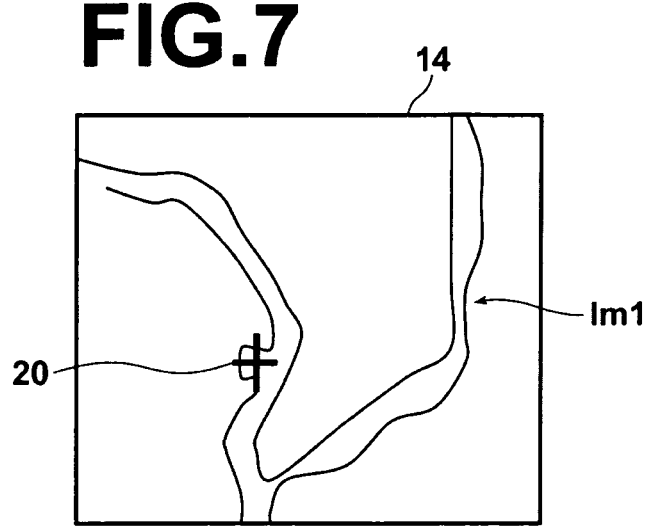
FIG. 7 illustrates a marker when an area of attention is specified in the point of attention tracking and displaying method according to the first embodiment of the present invention.

After the first projection direction vector Pv1, first projection plane P1, and projection target voxel are determined in Step S2, a first MIP image Im1 is generated on the first projection plane P1 in Step S3. By way of example, a specific method of generating a MIP image will be described in detail. First, the size of one pixel on the first projection plane P1 is determined. Here, a smallest size of actual dimensions of one voxel of the three-dimensional data M1 (which are assumed to be obtainable from imaging information of the three-dimensional image data M1) is used as the size of the length and width of one pixel on the projection plane P1. Then, an intersection between a line extended from the center voxel Vm1 to the first projection direction vector Pv1 and the first projection plane P1 is designated as pc1. Next, a maximum pixel value of those of voxels of the three-dimensional image data M1 on a straight line extended from pc1 to the reverse direction of the first projection direction vector Pv1 (from the projection plane toward the three-dimensional image data M1) is used as the pixel value of pc1. Similar processing is performed on each pixel of the first projection plane P1 from a pixel adjacent to pc1. In this way, the pixel value of each pixel on the first projection plane P1 is determined one after another, and when no voxel is present on the straight line extended from a pixel to the reverse direction of the first projection direction vector Pv1, the generation of the MIP image is completed. In this way, the first MIP image Im1 is generated (FIG. 7). When determining a maximum pixel value of those of voxels of the three-dimensional image data M1 on the straight line extended from each pixel on the projection plane P1 to the reverse direction of the first projection direction vector Pv1 as the pixel value of each pixel on the projection plane P1, the maximum pixel value may be selected from those of voxels through which the extended straight line passes in anyway or from those of voxels within in a predetermined distance from the extended straight line.

Figure 5:
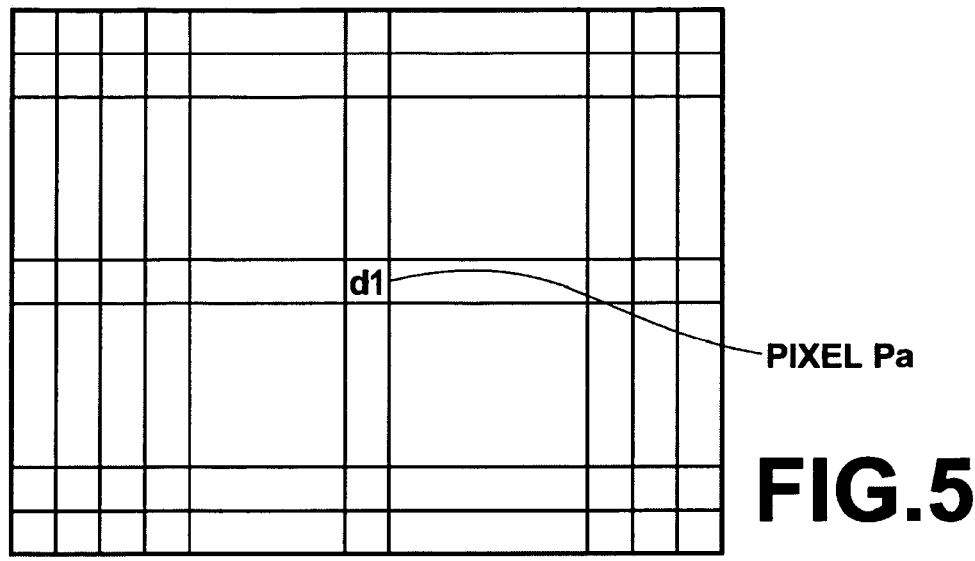
FIG. 5 is a drawing for explaining a Z-Buffer image in the point of attention tracking and displaying method according to the first embodiment of the present invention.
Figure 6:
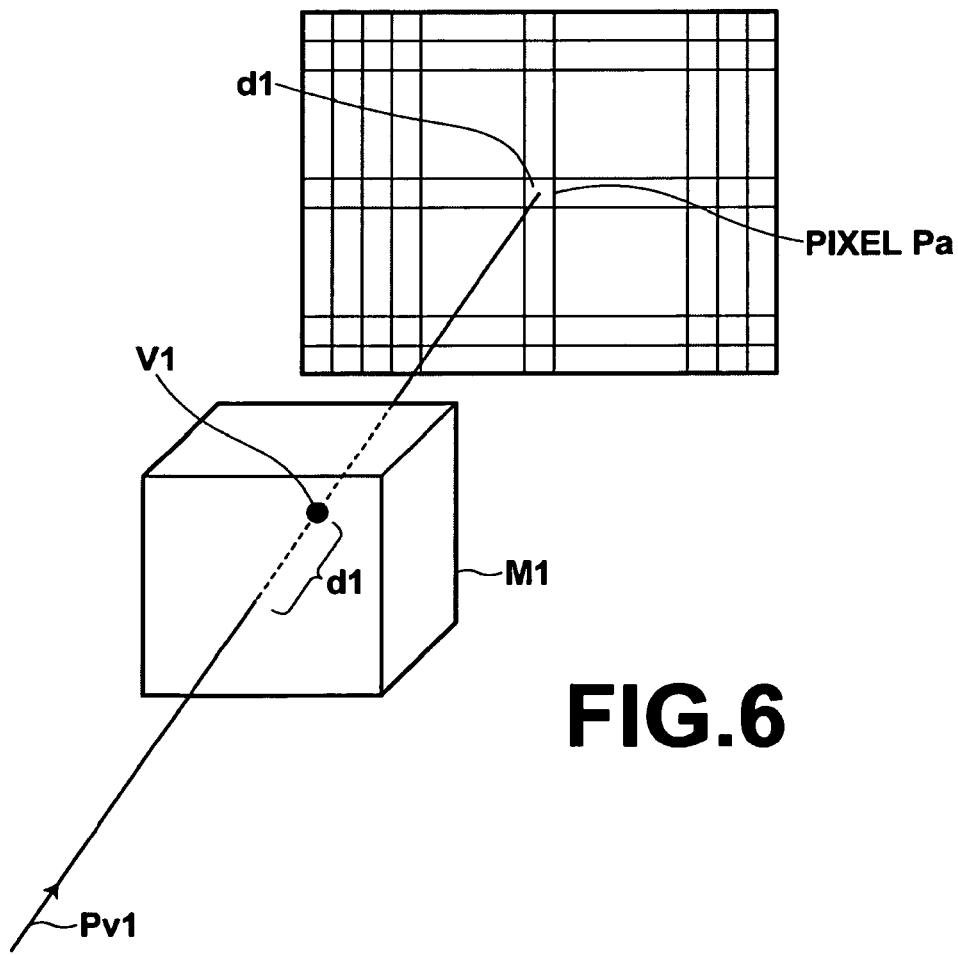
FIG. 6 is a drawing for explaining the relationship between a Z-Buffer image and a voxel of three-dimensional image data in the point of attention tracking and displaying method according to the first embodiment of the present invention.

In Step S3, a first Z-Buffer image ImZ1 is also generated in addition to the first MIP image Im1, as shown in FIG. 5. The first Z-Buffer image ImZ1 is an image having the same size (number of pixels) as that of the first MIP image Im1 with a distance, when a straight line is extended from the voxel whose pixel value is used as the pixel value of each pixel of the first MIP image Im1 to the reverse direction of the first projection direction vector Pv1 (opposite side to the first projection plane P1), from the voxel to the point of the projection target three-dimensional data at which the extended straight line exits from the data being used as the pixel value of each pixel. For example, with respect to the pixel Pa in the Z-Buffer image shown in FIG. 5, the distance, when a straight line is extended from the voxel V1, which served as the basis of the pixel value of the pixel Pa on the MIP image, to the reverse direction of the first projection direction vector Pv1, from the voxel V1 to the point of the three-dimensional image data M1 at which the extended straight line exits from the data M1 is d1, as shown in FIG. 6. Then, in Step S4, a point of attention, such as a point in a swelled area of a blood vessel, is specified by a doctor in the first MIP image Im1. Here, the coordinate position of the specified point in the first MIP image Im1 is designated as Q1. As for the method of specifying the point of attention, for example, a method in which a cursor is moved to the point of attention with mouse 12 in the first MIP image Im1 and the mouse is clicked may be conceivable. When the coordinate position Q1 is determined, marker 20 is displayed on the coordinate position Q1 in the first MIP image Im1, as shown in FIG. 7.

In Step S5, the coordinate position of voxel V1 in the three-dimensional image forming the pixel of the coordinate position Q1 in the first MIP image Im1 determined in Step S4 is calculated from the coordinate position Q1 in the first MIP image Im1, the first projection direction vector Pv1, and the first Z-Buffer image ImZ1. Here, the voxel V1 in the three-dimensional image forming the pixel of the coordinate position Q1 is obtained using the Z-Buffer image, but the voxel V1 may also be obtained by searching again for a voxel having a maximum pixel value of those of the three-dimensional image data M1 on a straight line extended from the coordinate position Q1 to the reverse direction of the first projection direction vector Pv1.

Figure 8:
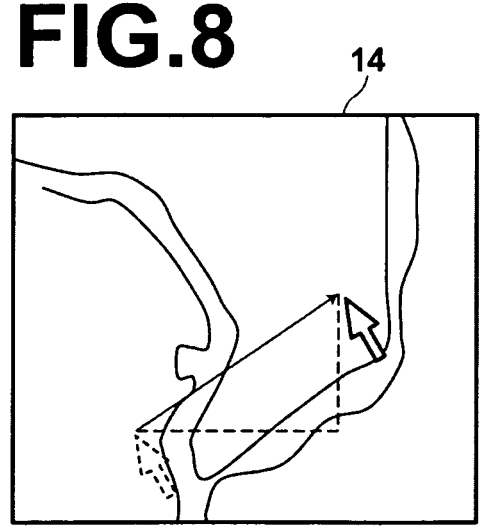
FIG. 8 is a drawing for explaining that a movement amount of projection direction is specified using a first MIP image.
Figure 9:
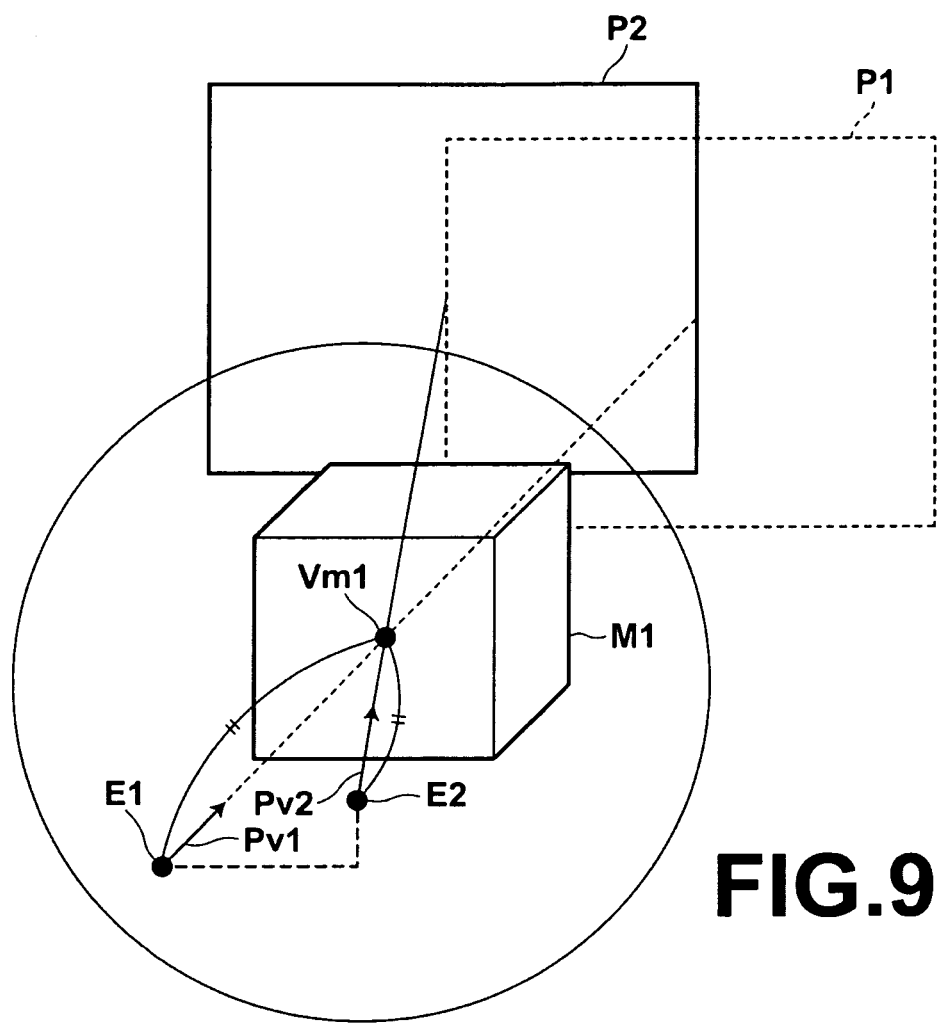
FIG. 9 is a drawing for explaining that a second imaging direction is determined from the movement amount of imaging direction specified by FIG. 8 in the point of attention tracking and displaying method according to the first embodiment of the present invention.

Then, in Step S6, in order to examine the swelled area of the blood vessel from a projection direction different from that of the first MIP image Im1, a second projection direction vector Pv2 is inputted by the doctor. Here, for the second projection direction vector Pv2, the vector value itself or an amount of change from the first projection direction vector Pv1 may be numerically inputted by keyboard 13, but an arrangement may be adopted in which the projection direction is changed by dragging the mouse on the displayed first projection image. For example, as shown in FIG. 8, when the mouse is dragged on the first projection image, a point E1 at a certain distance from the center Vm1 of the three-dimensional image data M1 in the reverse direction of the first projection direction vector Pv1 moves to a point E2 by maintaining the distance between the point E1 and Vm1 and the vector from point E2 toward the Vm1 is determined as the second projection direction vector Pv2, as shown in FIG. 9. When the second projection direction vector Pv2 is determined, a projection plane P2 with the second projection direction vector Pv2 as its normal is determined.

When the new projection direction vector Pv2 and projection plane P2 are determined in Step S6, a second MIP image Im2 and a second Z-Buffer image ImZ2 are generated in Step S7 in the same way as in Step S2.

Then, in Step S8, a coordinate Q2 of the voxel V1, which corresponds to the point of attention specified by the doctor, determined in Step S5 is obtained in the second MIP image Im2 generated based on the second projection direction vector Pv2 determined in Step S6.

Then, in Step S9, the coordinate of voxel V2 in the three-dimensional image forming the pixel of the coordinate Q2 in the second MIP image Im2 obtained in Step S8 is calculated from the second projection direction vector Pv2 and the second Z-Buffer image ImZ2 generated in Step S7.

Next, in Step S10, a determination is made as to whether or not the first voxel V1 and the second voxel V2 lie on the same coordinate position by making comparison between the coordinate positions of the two voxels. Note that the coordinate position of the first voxel V1 and the coordinate position of the second voxel V2 are not necessarily coincide exactly with each other and voxels V1 and V2 may be regarded as the same when they are in a predetermined distance.

In Step S10, if voxels V1 and V2 are determined to be the same, the second MIP image Im2 generated in Step S7 is displayed in Step S11 and further a marker is displayed on the coordinate position Q2 corresponding to the voxel V2 obtained in Step S9. Here, the marker has the same shape as that of the marker in Step S4, but displayed in a different color from that of the marker in Step S4 in order to indicate that the projection direction is different from that of the first MIP image Im1. An arrangement may be adopted here in which the marker is temporarily erased in order not to hinder the observation of the image by an operation of keyboard 12 or mouse 13.

In Step S10, if voxels V1 and V2 are determined not to be the same, the second MIP image Im2 generated in Step S7 is displayed in Step S12 and further a marker is displayed on the coordinate Q2 corresponding to the voxel V2 obtained in Step S9 in a blinking manner to indicate that the voxels are not the same. Here, the marker is displayed in the same shape but blinks in a different color from Step S4, as in Step S11. Here also, an arrangement may be adopted in which the marker is temporarily erased in order not to hinder the observation of the image by an operation of keyboard 12 or mouse 13. The markers have the same shape and different colors in the example described above, but they have different shapes and the same color or different shapes and colors.

In the present embodiment, the voxel V1 in the three-dimensional image data M1 corresponding to the coordinate position Q1 specified in the first MIP image Im1 is obtained, and the coordinate position Q2 which is the voxel V1 projected onto the second projection plane P2 in the second projection direction vector Pv2 is obtained. But the coordinate position Q2 in the second MIP image Im2 may be directly obtained without obtaining the voxel V1 based on the coordinate position Q1 in the first MIP image Im1, the inverse matrix of the projection matrix for projecting the three-dimensional image data M1 onto the first projection plane from the first projection direction vector Pv1, the projection matrix B for projecting the three-dimensional image data M1 onto the second projection plane P2 in the second projection direction vector Pv2, and the first Z-Buffer image ImZ1.

As described above, according to the present embodiment, one point in an area of attention specified in the first MIP image Im1 generated from the first projection direction is projected onto the second MIP image Im2 generated from a projection direction different from that of the first MIP image Im1, whereby the area of attention is tracked and displayed. This allows the doctor to know the position of the area of attention in the second MIP image Im2 and whether or not the point of attention in the first MIP image Im1 is displayed in the second MIP image Im2. In this way the present invention may provide useful information for understanding the three-dimensional positional relationship of organs or tissues of attention.

In the embodiment described above, a description has been made of a case in which a three-dimensional shape of a brain blood vessel is observed by a doctor using an image projected by maximum intensity projection from a plurality of brain tomographic images in a body axis direction obtained by MRI. The present invention may provide similar advantageous effects, for example, when a minimum value projection image is generated from a plurality of bronchi tomographic images in a body axis direction obtained by CT. Further, the projection method may be changed according to the projection direction like, for example, the maximum intensity project is used for a first projection direction while the minimum intensity project is used for a second projection direction. Still further, the projection image projected in the second projection direction may be a raysum image obtained by dividing the total of density values of voxels of three-dimensional image data on a straight line extended from each pixel on the second projection plane to the reverse direction of the second projection direction vector by the number of voxels. In this case, however, the voxel corresponding to the pixel of attention in the image generated from the first projection direction vector is not displayed in the image generated from the second projection direction vector, so that when the coordinate Q2 is obtained in Step S8, steps from Step S9 onward are not performed and only the position of the coordinate Q2 is displayed.

The invention claimed is:

1. A projection image generation apparatus for generating a projection image by processing three-dimensional image data obtained by reconstructing multiple two-dimensional images, the apparatus comprising:
   a first projection target determination means for determining first three-dimensional image data to be projected from the three-dimensional image data;
   a first projection image generation means for generating a first projection image by projecting the first three-dimensional image data in a first projection direction by maximum intensity projection or minimum intensity projection;
   a first coordinate specifying means for specifying a first coordinate position in the first projection image;
   a second projection target determination means for determining second three-dimensional image data to be projected from the three-dimensional image data;
   a second projection image generation means for generating a second projection image by projecting the second three-dimensional image data in a second projection direction different from the first projection direction; and
   a second coordinate display means for displaying a second coordinate position, in the second projection image, obtained by projecting a first voxel in the three-dimensional image data, which corresponds to the pixel at the first coordinate position in the first projection image, onto the second projection image in the second projection direction,
   wherein the second projection image generation means is a means that generates a projection image by maximum intensity projection,
   wherein the second coordinate display means is a means that, when the first voxel and a second voxel in the three-dimensional image data corresponding to the pixel at the second coordinate position in the second projection image are different, indicates that the first voxel and the second voxel are different, and
   wherein the second coordinate display means displays a marker at the second coordinate position, and displays the marker in a different manner in the case that the first voxel and the second voxel are different.

2. The projection image generation apparatus of claim 1, wherein the second coordinate display means is a means that determines the first voxel from a Z-Buffer image generated with the first projection image in advance and the first coordinate position, and displays the second coordinate position obtained by projecting the first voxel onto the second projection image in the second projection direction.

3. The projection image generation apparatus of claim 1, wherein the second coordinate display means is a means that obtains the second coordinate position from a Z-Buffer image generated with the first projection image in advance, a transformation matrix for generating the first projection image from the first three-dimensional image data, a transformation matrix for generating the second projection image from the second three-dimensional image data, and the specified first coordinate position, and displays the obtained second coordinate position.

4. The projection image generation apparatus of claim 1, wherein the second projection target determination means is a means that determines the first three-dimensional image data determined by the first projection target determination means as the second three-dimensional image data.

5. A projection image generation method for generating a projection image by processing three-dimensional image data obtained by reconstructing multiple two-dimensional images, the method comprising the steps of:

determining first three-dimensional image data to be projected from the three-dimensional image data;

generating a first projection image by projecting the first three-dimensional image data in a first projection direction by maximum intensity projection or minimum intensity projection;

specifying a first coordinate position in the first projection image;

determining second three-dimensional image data to be projected from the three-dimensional image data;

generating a second projection image by projecting the second three-dimensional image data in a second projection direction different from the first projection direction; and displaying a second coordinate position, in the second projection image, obtained by projecting a first voxel in the three-dimensional image data, which corresponds to the pixel at the first coordinate position in the first projection image, onto the second projection image in the second projection direction, wherein the step of generating a second projection image generates a projection image by maximum intensity projection, wherein the step of displaying a second coordinate position, when the first voxel and a second voxel in the three-dimensional image data corresponding to the pixel at the second coordinate position in the second projection image are different, indicates that the first voxel and the second voxel are different, and wherein the step of displaying a second coordinate position displays a marker at the second coordinate position, and displays the marker in a different manner in the case that the first voxel and the second voxel are different.

6. A non-transitory computer readable recording medium on which is recorded a program for causing a computer to perform the steps of:

determining first three-dimensional image data to be projected from three-dimensional image data obtained by reconstructing multiple two-dimensional images;

generating a first projection image by projecting the first three-dimensional image data in a first projection direction by maximum intensity projection or minimum intensity projection;

specifying a first coordinate position in the first projection image;

determining second three-dimensional image data to be projected from the three-dimensional image data;

generating a second projection image by projecting the second three-dimensional image data in a second projection direction different from the first projection direction; and displaying a second coordinate position, in the second projection image, obtained by projecting a first voxel in the three-dimensional image data, which corresponds to the pixel at the first coordinate position in the first projection image, onto the second projection image in the second projection direction, wherein the step of generating a second projection image generates a projection image by maximum intensity projection, wherein the step of displaying a second coordinate position, when the first voxel and a second voxel in the three-dimensional image data corresponding to the pixel at the second coordinate position in the second projection image are different, indicates that the first voxel and the second voxel are different, and wherein the step of displaying a second coordinate position displays a marker at the second coordinate position, and displays the marker in a different manner in the case that the first voxel and the second voxel are different.

7. A projection image generation apparatus for generating a projection image by processing three-dimensional image data obtained by reconstructing multiple two-dimensional images, the apparatus comprising:

a first projection target determination means for determining first three-dimensional image data to be projected from the three-dimensional image data;

a first projection image generation means for generating a first projection image by projecting the first three-dimensional image data in a first projection direction by maximum intensity projection or minimum intensity projection;

a first coordinate specifying means for specifying a first coordinate position in the first projection image;

a second projection target determination means for determining second three-dimensional image data to be projected from the three-dimensional image data;

a second projection image generation means for generating a second projection image by projecting the second three-dimensional image data in a second projection direction different from the first projection direction; and a second coordinate display means for displaying a second coordinate position, in the second projection image, obtained by projecting a first voxel in the three-dimensional image data, which corresponds to the pixel at the first coordinate position in the first projection image, onto the second projection image in the second projection direction, wherein the second projection image generation means is a means that generates a projection image by minimum intensity projection, wherein the second coordinate display means is a means that, when the first voxel and a second voxel in the three-dimensional image data corresponding to the pixel at the second coordinate position in the second projection image are different, indicates that the first voxel and the second voxel are different, and wherein the second coordinate display means displays a marker at the second coordinate position, and displays the marker in a different manner in the case that the first voxel and the second voxel are different.

8. A projection image generation method for generating a projection image by processing three-dimensional image data obtained by reconstructing multiple two-dimensional images, the method comprising the steps of:

determining first three-dimensional image data to be projected from the three-dimensional image data;

generating a first projection image by projecting the first three-dimensional image data in a first projection direction by maximum intensity projection or minimum intensity projection;

specifying a first coordinate position in the first projection image;

determining second three-dimensional image data to be projected from the three-dimensional image data;

generating a second projection image by projecting the second three-dimensional image data in a second projection direction different from the first projection direction; and displaying a second coordinate position, in the second projection image, obtained by projecting a first voxel in the three-dimensional image data, which corresponds to the pixel at the first coordinate position in the first projection image, onto the second projection image in the second projection direction, wherein the step of generating a second projection image generates a projection image by minimum intensity projection, wherein the step of displaying a second coordinate position, when the first voxel and a second voxel in the three-dimensional image data corresponding to the pixel at the second coordinate position in the second projection image are different, indicates that the first voxel and the second voxel are different, and wherein the step of displaying a second coordinate position displays a marker at the second coordinate position, and displays the marker in a different manner in the case that the first voxel and the second voxel are different.

9. A non-transitory computer readable recording medium on which is recorded a program for causing a computer to perform the steps of:

determining first three-dimensional image data to be projected from three-dimensional image data obtained by reconstructing multiple two-dimensional images;

generating a first projection image by projecting the first three-dimensional image data in a first projection direction by maximum intensity projection or minimum intensity projection;

specifying a first coordinate position in the first projection image;

determining second three-dimensional image data to be projected from the three-dimensional image data;

generating a second projection image by projecting the second three-dimensional image data in a second projection direction different from the first projection direction; and displaying a second coordinate position, in the second projection image, obtained by projecting a first voxel in the three-dimensional image data, which corresponds to the pixel at the first coordinate position in the first projection image, onto the second projection image in the second projection direction, wherein the step of generating a second projection image generates a projection image by minimum intensity projection, wherein the step of displaying a second coordinate position, when the first voxel and a second voxel in the three-dimensional image data corresponding to the pixel at the second coordinate position in the second projection image are different, indicates that the first voxel and the second voxel are different, and wherein the step of displaying a second coordinate position displays a marker at the second coordinate position, and displays the marker in a different manner in the case that the first voxel and the second voxel are different.

* * * * *